United States Patent [19]

Shima et al.

[11] Patent Number: 4,616,083

[45] Date of Patent: * Oct. 7, 1986

[54] STABLE ANTIBACTERIAL LYOPHILIZATES

[75] Inventors: Kazuhiro Shima, Nara; Masayoshi Inoue, Osaka; Takayuki Tsukada, Hyogo, all of Japan

[73] Assignee: Shionogi & Co., Ltd., Osaka, Japan

[ * ] Notice: The portion of the term of this patent subsequent to Jul. 30, 2002 has been disclaimed.

[21] Appl. No.: 641,821

[22] Filed: Aug. 17, 1984

[30] Foreign Application Priority Data

Aug. 22, 1983 [JP] Japan ................... 58-153938

[51] Int. Cl.$^4$ .............................. C07D 498/04
[52] U.S. Cl. ..................................... 544/90
[58] Field of Search ........................... 544/90

[56] References Cited

U.S. PATENT DOCUMENTS 4,532,233  7/1985  Tsuji et al. ................ 544/90 X

FOREIGN PATENT DOCUMENTS 57234472  8/1984  Japan .
2078737  1/1982  United Kingdom .

Primary Examiner—Richard L. Raymond
Attorney, Agent, or Firm—Wenderoth, Lind & Ponack

[57] ABSTRACT

A lyophilized preparation of 7$\beta$-difluoromethylthioacetamido-7$\alpha$-methoxy-3-[1-(2-hydroxyalkyl)-1H-tetrazol-5-yl]-thiomethyl-1-dethia-1-oxa-3-cephem-4-carboxylic acid alkali metal salt containing glucose, fructose, maltose, or an alkali metal salt of mineral acid or carboxylic acid as a stabilizer.

5 Claims, No Drawings

STABLE ANTIBACTERIAL LYOPHILIZATES

This invention relates to a stable lyophilized preparation of an antibacterial, 7β-difluoromethylthioacetamido-7α-methoxy-3-[1-(2-hydroxyalkyl)-1H-tetrazol-5-yl]thiomethyl-1-dethia-1-oxa-3-cephem-4-carboxylic acid alkali metal salt (I):

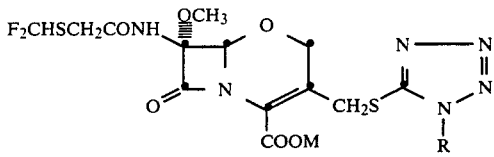

(where R is 2-hydroxyalkyl and M is alkali metal) containing as a stabilizer or color preventing agent at least one material selected from the group consisting of glucose, fructose, maltose, and an alkali metal salt of mineral acid or carboxylic acid.

In the formula (I), preferable R groups are 2 to 4C 2-hydroxyalkyl, especialy 2-hydroxyethyl and 2-hydroxypropyl. Preferable as M are sodium and potasium.

The said Compound (I) (described in Japanese Patent Application No. 57-234,472 and U.S. Pat. No. 4,532,233) shows a strong antibacterial potency against Gram-positive and -negative bacteria and is useful as a medicine. When the compound is lyophilized conventionally for medical use, the product slowly develops yellowish brown color and deteriorates in its antibacterial potency.

The present inventors sought to overcome this defect and found that the said stabilizer or color preventing reagent is effective.

It has been disclosed that sugar and sugar alcohol are effective for stabilizing a lyophilized preparation of some beta-lactam antibacterials (Japanese Patent Kokai 57-11909), but mannitol, the most effective in that case, is ineffective for stabilizing the present Compound (I). Among the sugars, effectives ones for stabilizing Compound (I) are only glucose, fructose, and maltose. Said alkali metal salt of mineral acid is preferably that of hydrochloric acid, sulfuric acid, sulfurous acid, phosphoric acid, or the like, especially non-toxic sodium or potassium salt. The said alkali metal salt of carboxylic acid is preferably alkali metal salt of 3 to 6C dibasic aliphatic carboxylic acid (succinic, maleic, fumaric, or the like acids), especially non-toxic sodium or potassium salt.

The lyophilized preparation of this invention is produced as follows:

Compound (I) and the said stabilizer are dissolved in an aqueous solvent to give a mixed solution, if required adjusting its pH at 5 to 8, cooled to freeze the solution rapidly at −10° to −60° C. over 2 minutes to 10 hours, and, if required under supplying sublimation heat, dried by sublimating water at 0.005 to 1 millibar over 5 to 72 hours until the objective water content is achieved. The product is preferably sealed and stored in a container, if required filled with an inert gas, e.g., nitrogen, dry air.

Mechanical mixing of lyophilized Compound (I) and the said stabilizer does not stabilize the Compound (I).

This preparation is usually produced by conventional tray-, spray-, vial-, or the like lyophilization method.

The amount of said stabilizer is 0.01 to 0.5, especially 0.02 to 0.3, parts by weight of Compound (I) to prevent the decomposition and color development. In the preparation, either Compound (I) or stabilizer usually shows no crystalline structure observable in its X-ray diffraction pattern.

The thus produced preparation is highly soluble in water, easily produced sanitarily and ecologically, and is suitable as medicines for various injections. Further, it is suitable as bulk material for long term storage.

Said sterile preparation can be dissolved in a vehicle for injection before use and administered conventionally intravenously or intramuscularly.

The following examples illustrate embodiments of this invention.

EXAMPLE 1

A solution of Compound (I) (M=Na, R=CH$_2$CH$_2$OH) (1 g) and stabilizer (glucose, fructose, or maltose) (0.3 g) in sterile distilled water for injection (4 ml) is poured into a 10 ml vial and cooled rapidly to −35° C. in a refrigerator. After keeping at −35° C. for 3 hours, the frozen mass is lyophilized at 0.1 mb for 20 hours and 0.05 mb or below for 6 hours at a temperature lower than −20° C. to sublimate contained water affording a stable lyophilizate.

EXAMPLE 2

Substituting the stabilizer with 2 w/w % of sodium hydrogen sulfite, sodium sulfate, or sodium chloride, the method of Example 1 is repeated to give a stable preparation.

EXAMPLE 3

Substituting the stabilizer with ¼ millimole of sodium succinate, sodium fumarate, or sodium maleate, the method of Example 1 is repeated to afford a stable preparation.

EXAMPLE 4

Substituting the amount of stabilizer by 0.1 g, amount of sterile water by 10 ml, volume of vial by 100 ml, freezing by −40° C. for 2 hours, and sublimation by 0.05 mb for 10 hours and 0.005 mb for 10 hours, the method of Example 1 is repeated to afford a stable preparation.

EXAMPLE 5

Substituting the amount of stabilizer by 0.5 g, the method of Example 4 is repeated to afford a stable preparation.

TABLE

| Stability of lyophilized preparation of Examples 1–3 | | |
|---|---|---|
| Stabilizer | Amount vs 1g of Compd. (I) | Potency (50° C., 1 month) |
| Glucose | 30 (w/w %) | 89.1 (%) |
| Fructose | " | 86.6 |
| Maltose | " | 89.3 |
| NaHSO$_3$ | 2 (w/w %) | 85.5 |
| Na$_2$SO$_4$ | " | 84.7 |
| NaCl | " | 86.8 |
| Na succinate | 0.25 (mM) | 86.0 |
| Na fumarate | " | 85.3 |
| Na maleate | " | 86.4 |
| Reference | — | 83.3 |

EXAMPLE 6

Substituting the amount of stabilizer by 1 w/w % or 10 w/w %, freezing by −28° C. for 5 hours, and sublimation by 0.5 mb for 10 hours and 0.1 mb for 20 hours, the method of Example 2 is repeated to afford a stable preparation.

EXAMPLE 7

Substituting the amount of stabilizer by 5 w/w % or 8 w/w %, amount of sterile water by 10 ml, volume of vial by 100 ml, freezing by −30° C. for 4 hour 15 minutes, and sublimation at 0.2 mb for 24 hours and 0.04 mb for 8 hours, the method of Example 2 is repeated to afford a stable preparation.

EXAMPLE 8

Substituting the amount of stabilizer by ½ millimoles or 1 millimole, the method of Example 3 is repeated to afford a stable preparation.

EXAMPLE 9

Each 10 amounts of Compound (I, M=K, R=—CH$_2$CH(CH$_3$)OH), the stabilizer, and sterile water as much as those of Example 3 are mixed to make a solution. Its pH is adjusted at 6.7 with phosphate buffer and the neutral solution is poured into a lyophile tray, and lyophilized under the condition of Example 3 to afford a bulk of stable lyophilized preparation.

Lyophilizates of Examples 1 to 9 do not show yellowish brown color as observable in the case of lyophilized material containing none of said stabilizers. In a test at 50° C., the stable lyophilizate did not develop color deeper than pale yellow up to 3 months and retained its antibacterial potency up to 95% up to 1 month.

EXPERIMENT

A solution of sterile product of Examples 1 to 3 in distilled water for injection (4 ml) is administered by intravenous injection or drip to a patient suffering from *Staphylococcus aureus* infection thrice a day to treat the infection.

What we claim is:

1. A lyophilized preparation of an antibacterial, 7β-difluoromethylthioacetamido-7α-methoxy-3-[1-(2-hydroxyalkyl)-1H-tetrazol-5-yl]thiomethyl-1-dethia-1-oxa-3-cephem-4-carboxylic acid alkali metal salt, containing, as a stabilizer, an alkali metal salt of a mineral acid.

2. A preparation as claimed in claim 1, where the antibacterial is 7β-difluoromethylthioacetamido-7α-methoxy-3-[1-(2-hydroxyethyl)-1H-tetrazol-5-yl)thiomethyl-1-dethia-1-oxa-3-cephem-4-carboxylic acid sodium salt.

3. A preparation as claimed in claim 1, where the stabilizer is sodium hydrogen sulfite, sodium sulfate, or sodium chloride.

4. A preparation as claimed in claim 1, where ratio of the stabilizer and the antibacterial is between 0.01 and 0.5 parts by weight.

5. A preparation claimed in claim 4, where the ratio is between 0.02 and 0.3 parts by weight.

* * * * *